US011938275B2

United States Patent
Gurumoorthy

(10) Patent No.: US 11,938,275 B2
(45) Date of Patent: Mar. 26, 2024

(54) SYSTEMS, METHODS, AND DEVICES FOR CUSTOM SLEEP IMPLEMENTATION

(71) Applicant: StimScience Inc., Berkeley, CA (US)

(72) Inventor: Ram Gurumoorthy, Lafayette, CA (US)

(73) Assignee: STIMSCIENCE INC., Berkeley, CA (US)

( * ) Notice: Subject to any disclaimer, the term of this patent is extended or adjusted under 35 U.S.C. 154(b) by 201 days.

(21) Appl. No.: 17/000,220

(22) Filed: Aug. 21, 2020

(65) Prior Publication Data

US 2022/0054795 A1 Feb. 24, 2022

(51) Int. Cl.
  *A61B 5/00* (2006.01)
  *A61M 21/02* (2006.01)
  *A61M 21/00* (2006.01)

(52) U.S. Cl.
  CPC .......... *A61M 21/02* (2013.01); *A61B 5/4812* (2013.01); *A61B 5/4815* (2013.01); *A61B 5/4857* (2013.01); *A61B 5/7475* (2013.01); *A61M 2021/0022* (2013.01); *A61M 2021/0027* (2013.01); *A61M 2021/0044* (2013.01); *A61M 2021/0055* (2013.01); *A61M 2021/0072* (2013.01); *A61M 2230/04* (2013.01);
  (Continued)

(58) Field of Classification Search
  CPC ..... A61M 21/02; A61B 5/4812; A61B 5/4815
  See application file for complete search history.

(56) References Cited

U.S. PATENT DOCUMENTS

2010/0197996 A1* 8/2010 Cornel ................. A61M 21/00 600/28
2011/0018720 A1* 1/2011 Rai ...................... A61B 5/4812 340/575
(Continued)

FOREIGN PATENT DOCUMENTS

JP 2018517995 A 7/2018
JP 2020129188 A 8/2020

OTHER PUBLICATIONS

Zambotti et al. "Magnitude of the impact of hot flashes on sleep in perimenopausal women." Fertility and sterility vol. 102,6: 1708-15 .e1. doi: 10.1016/j.fertnstert.2014.08.016 (Year: 2014).*
(Continued)

Primary Examiner — Kaylee R Wilson
(74) Attorney, Agent, or Firm — SCHWEGMAN LUNDBERG & WOESSNER, P.A.

(57) ABSTRACT

Provided are systems, methods, and devices for implementation of custom sleep parameters. Methods include receiving, via a user interface, a plurality of input parameters associated with a sleep profile of a user, the plurality of input parameters representing at least one sleep profile target, generating, using one or more processors of a processing device, a plurality of sleep parameters based, at least in part, on the received plurality of input parameters, the plurality of sleep parameters representing one or more changes to one or more biomarkers of the user, and generating, using one or more processors of the processing device, a plurality of stimulation parameters based, at least in part, on the plurality of sleep parameters, the plurality of stimulation parameters representing stimuli configured to implement the identified changes for each of the identified biomarkers of the user's sleep profile.

29 Claims, 6 Drawing Sheets

(52) U.S. Cl.
CPC ..... *A61M 2230/10* (2013.01); *A61M 2230/18* (2013.01); *A61M 2230/50* (2013.01)

(56) References Cited

U.S. PATENT DOCUMENTS

| | | |
|---|---|---|
| 2013/0303837 A1 | 11/2013 | Berka et al. |
| 2014/0316191 A1 | 10/2014 | Zambotti et al. |
| 2016/0176409 A1* | 6/2016 | Kirsch ............... B60N 2/02 701/1 |
| 2016/0270717 A1* | 9/2016 | Luna .................. A61B 5/743 |
| 2017/0000970 A1 | 1/2017 | Molina et al. |
| 2019/0099009 A1* | 4/2019 | Connor ............... A61B 5/398 |
| 2019/0126033 A1* | 5/2019 | Pradeep ........... A61N 1/36025 |
| 2019/0231256 A1* | 8/2019 | Jantunen ........... A61B 5/4815 |
| 2019/0282812 A1* | 9/2019 | Simons .............. A61N 1/20 |
| 2020/0113344 A1* | 4/2020 | Youngblood ....... A61B 5/4815 |
| 2020/0234814 A1* | 7/2020 | Theory ............... G16H 20/70 |
| 2022/0059210 A1 | 2/2022 | Gurumoorthy |

OTHER PUBLICATIONS

European Application Serial No. 21192253.9, Search Report dated Jan. 31, 22, 11 pgs.
"International Application Serial No. PCT/US2022/071989, International Search Report dated Aug. 18, 2022", 12 pgs.
"International Application Serial No. PCT/US2022/071989, Written Opinion dated Aug. 18, 2022", 4 pgs.

\* cited by examiner

SYSTEMS, METHODS, AND DEVICES FOR CUSTOM SLEEP IMPLEMENTATION

TECHNICAL FIELD

The present disclosure relates to mechanisms and processes directed to measurements of brain activity and the implementation of custom sleep parameters.

BACKGROUND

Human sleep can be measured using several aspects of the human physiology including their brain activity, their heart activity, their eye activity, temperature, movement, oxygen saturation, and the like. A human brain may include neurons which exhibit measurable electrical signals when active. Accordingly, various measuring modalities, such as electrodes, may be used to measure such electrical activity. The neural activity of neurons may include many a variety of frequency components. Accordingly, such electrical activity may be measured and represented as a power spectrum in a frequency domain. Moreover, such measurements may be obtained as a user sleeps. Similarly, other measurements may be obtained, such as heart rate activity that includes a heart rate (mean, minimum or maximum over a period, mean square over a period), as well as heart rate variability (beat-to-beat, or beat-to-beat aggregated over a window of time). However, traditional techniques for measuring such electrical activity in such contexts remain limited in their ability to utilize such measurements, and more specifically, to efficiently and effectively enable custom tailoring of a user's sleep parameters.

SUMMARY

Provided are systems, methods, and devices for the implementation of custom sleep parameters. Methods include receiving, via a user interface, a plurality of input parameters associated with a sleep profile of a user, the plurality of input parameters representing at least one sleep profile target, generating, using one or more processors of a processing device, a plurality of sleep parameters based, at least in part, on the received plurality of input parameters, the plurality of sleep parameters representing one or more changes to one or more biomarkers of the user, and generating, using one or more processors of the processing device, a plurality of stimulation parameters based, at least in part, on the plurality of sleep parameters, the plurality of stimulation parameters representing stimuli configured to implement the identified changes for each of the identified biomarkers of the user's sleep profile.

In some embodiments, the methods further include mapping the plurality of input parameters to a plurality of target parameters, the plurality of target parameters identifying the one or more biomarkers of the user. In various embodiments, the mapping is generated based, at least in part, on previous measurement data. According to some embodiments, the one or more changes represented by the plurality of sleep parameters are configured to identify target values for the one or more biomarkers. In some embodiments, the identified biomarkers include a ratio of band activities, shifts in frequency spectra of activity, and a dominant rational map of the user. In various embodiments, the plurality of stimulation parameters is configured to change each of one or more current values of the one or more biomarkers to the identified target values of the one or more biomarkers. According to some embodiments, the methods further include applying stimuli to the user based, at least in part, on the stimulation parameters, and receiving measurement data based, at least in part, on the applying of the stimuli. In some embodiments, the methods further include generating a result object based, at least in part, on the measurement data, the result object representing an efficacy of the stimulation parameters. In various embodiments, the efficacy of the stimulation parameters is determined based, at least in part, on the at least one sleep profile target.

Also disclosed herein are systems including a communications interface configured to receive a plurality of input parameters associated with a sleep profile of a user, the plurality of input parameters representing at least one sleep profile target. Systems further include a processing device configured to generate a plurality of sleep parameters based, at least in part, on the received plurality of input parameters, the plurality of sleep parameters representing one or more changes to one or more biomarkers of the user, generate a plurality of stimulation parameters based, at least in part, on the plurality of sleep parameters, the plurality of stimulation parameters representing stimuli configured to implement the identified changes for each of the identified biomarkers of the user's sleep profile, and a memory device configured to store the plurality of sleep parameters and the plurality of stimulation parameters.

In some embodiments, the processing device is further configured to map the plurality of input parameters to a plurality of target parameters, the plurality of target parameters identifying the one or more biomarkers of the user. In various embodiments, the one or more changes represented by the plurality of sleep parameters are configured to identify target values for the one or more biomarkers. According to some embodiments, the plurality of stimulation parameters is configured to change each of one or more current values of the one or more biomarkers to the identified target values of the one or more biomarkers. In some embodiments, the processing device is further configured to apply stimuli to the user based, at least in part, on the stimulation parameters, receive measurement data based on the applying of the stimuli, and generate a result object based, at least in part, on the measurement data, the result object representing an efficacy of the stimulation parameters. In various embodiments, the efficacy of the stimulation parameters is determined based, at least in part, on the at least one sleep profile target.

Further disclosed herein are devices that include a communications interface configured to receive a plurality of input parameters associated with a sleep profile of a user, the plurality of input parameters representing at least one sleep profile target. The devices further include one or more processors configured to generate a plurality of sleep parameters based, at least in part, on the received plurality of input parameters, the plurality of sleep parameters representing one or more changes to one or more biomarkers of the user, and generate a plurality of stimulation parameters based, at least in part, on the plurality of sleep parameters, the plurality of stimulation parameters representing stimuli configured to implement the identified changes for each of the identified biomarkers of the user's sleep profile.

In some embodiments, the one or more processors are further configured to map the plurality of input parameters to a plurality of target parameters, the plurality of target parameters identifying the one or more biomarkers of the user. In various embodiments, the one or more changes represented by the plurality of sleep parameters are configured to identify target values for the one or more biomarkers. According to some embodiments, the plurality of stimulation parameters is configured to change each of one or more current values of the one or more biomarkers to the identified target values of the one or more biomarkers. In some embodiments, the one or more processors are further configured to apply stimuli to the user based, at least in part, on the stimulation parameters, receive measurement data based on the applying of the stimuli, and generate a result object based, at least in part, on the measurement data, the result object representing an efficacy of the stimulation parameters.

These and other embodiments are described further below with reference to the figures.

DETAILED DESCRIPTION OF EXAMPLE EMBODIMENTS

Reference will now be made in detail to some specific examples including the best modes contemplated by the inventors. Examples of these specific embodiments are illustrated in the accompanying drawings. While the present disclosure is described in conjunction with these specific embodiments, it will be understood that it is not intended to limit the disclosure to the described embodiments. On the contrary, it is intended to cover alternatives, modifications, and equivalents as may be included within the spirit and scope of the disclosure as defined by the appended claims. In addition, although many of the components and processes are described below in the singular for convenience, it will be appreciated by one of skill in the art that multiple components and repeated processes can also be used to practice the techniques of the present disclosure.

In the following description, numerous specific details are set forth in order to provide a thorough understanding of the present invention. Particular embodiments may be implemented without some or all of these specific details. In other instances, well known process operations have not been described in detail in order not to unnecessarily obscure the disclosure.

Figure 1:
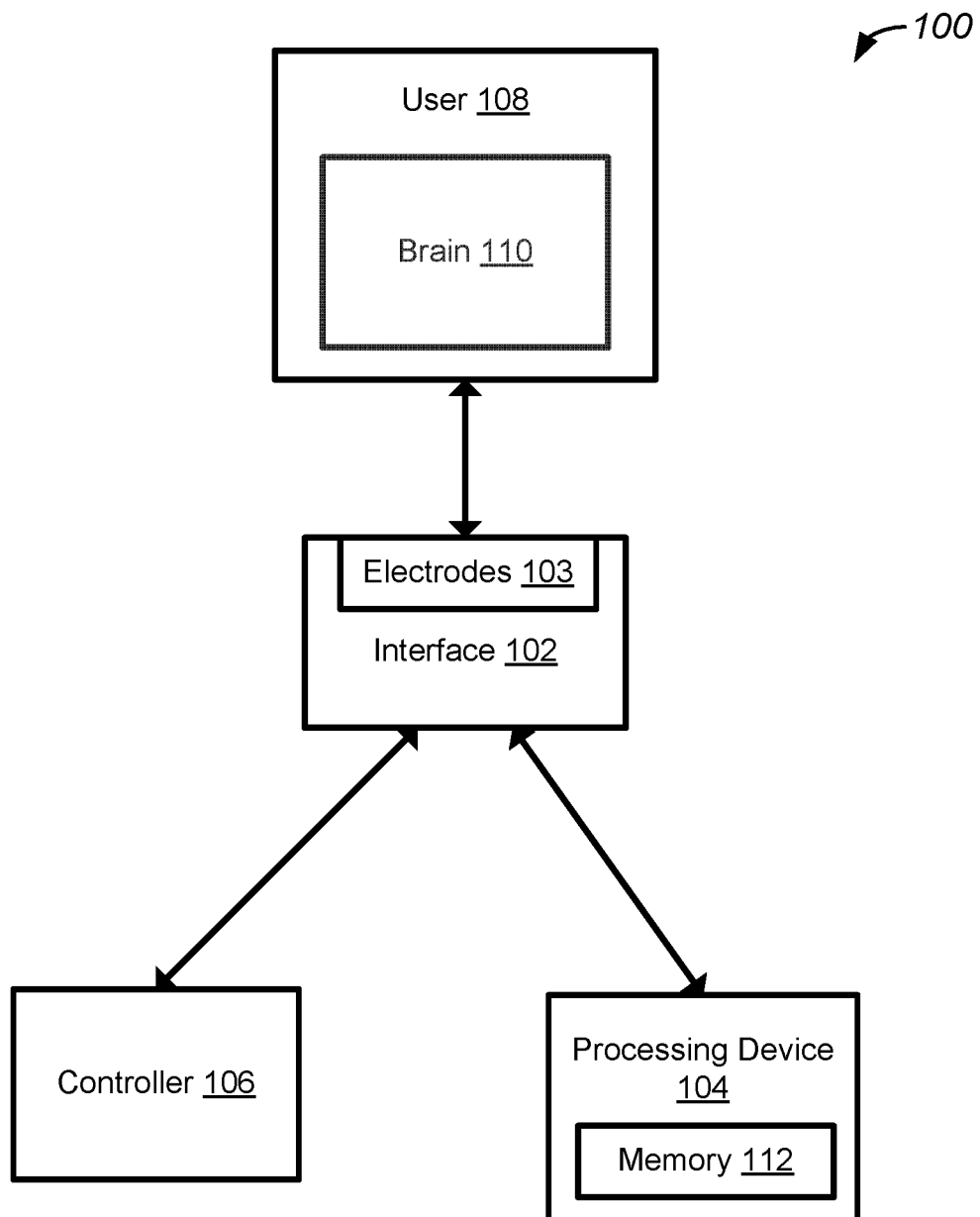
FIG. 1 illustrates an example of a system for the implementation of custom sleep parameters, configured in accordance with some embodiments.

FIG. 1 illustrates an example of a system for the implementation of custom sleep parameters, configured in accordance with some embodiments. As will be discussed in greater detail below, systems, such as system 100, may enable a user to identify target goals for their sleep profile, and subsequently have a stimulation program generated that is specifically configured to the user and the user's sleep profile, and configured to implement the identified changes to achieve the target goals for their sleep profile.

As will be discussed in greater detail below, components of system 100 may be implemented to generate custom stimulation programs to implement custom sleep targets for a user, such as user 108. As shown in FIG. 1, user 108 may be a person, and may be coupled to components of system 100. More specifically, brain 110 of user 108 may be coupled to system 100 such that system 100 is able to monitor and measure neural activity within brain 110. In some embodiments, the activity is electrical activity that is measured and recorded as electrical measurements. In this way, activity within brain 110 may be monitored during a period of sleep. As will also be discussed in greater detail below, the coupling between user 108 and system 100 may also enable stimulation of neurons within brain 110. Accordingly, system 100 may also modify neural activity of user 108.

In various embodiments, coupling between user 108 and system 100 may be implemented, at least in part, via an interface, such as interface 102. In one example, interface 102 includes a plurality of electrodes. More specifically, such electrodes may be implemented as an electrode array. Such electrodes may be included in a scalp potential electroencephalogram (EEG) array, may be deep brain stimulation (DBS) electrodes such as electrodes used with intracranial electroencephalography, or may be an epidural grid of electrodes. In other examples, the electrodes may include optogenetics mechanisms for monitoring various neuronal processes or blood saturation. Mechanisms may be used to make various measurements and acquire measurement signals corresponding to neural activity, heart activity, temperature, body/head/eye movements. As used herein, neural activity may refer to spiking or non-spiking activity/potentiation. Moreover, heart activity may be a measure of beat rate or beat-to-beat variability. Furthermore, eye movements may include micro and macro saccades, as well as slow and rapid eye movements.

In various embodiments, such measured signals may be electrical signals derived based on neural activity that may occur in cortical tissue of a brain or may include electrical and optical signals derived from the peripheral parts of the user. Such measurements may be acquired and represented in a time domain and/or frequency domain. In this way, activity may be monitored and measured over one or more temporal windows, and such measurements may be stored and utilized by system 100. In various embodiments, such neural activity may be observed for particular regions of cortical tissue determined, at least in part, based on a configuration of interface 102. In one example, this may be determined based on a configuration and location of electrodes included in interface 102 and coupled with the brain.

According to some embodiments, one or more components of interface 102 are configured to provide stimuli to the brain coupled with interface 102. For example, one or more electrodes included in interface 102 may be configured to provide electrical stimuli to cortical tissue of the brain. As discussed above, such electrodes may be implemented utilizing one or more of various modalities which may be placed on a user's scalp, or implanted in the user's brain.

As will be discussed in greater detail below, such actuation and stimuli provided by interface 102 may be of many different modalities. For example, stimuli may be aural, visual, and/or tactile as well as being electrical and/or magnetic, or any suitable combination of these. Accordingly, interface 102 may further includes additional components, such as speakers, lights, display screens, and mechanical actuators that are configured to provide one or more of aural, visual, and/or tactile stimuli to a user. In this way, any suitable combination of different modalities may be used.

For example, a combination of electrical and aural stimuli may be provided via interface 102. Further still, interface 102 may include different portions corresponding to signal acquisition and stimuli administration. For example, a first portion of interface 102 may include electrodes configured to measure neural activity, while a second portion of interface 102 includes speakers configured to generate aural stimuli. In another example, a third portion of interface 102 may include electrodes to measure ECG or heart rate, while a fourth portion may include sensors to measure oxygen saturation.

In some embodiments, interface 102 further includes one or more dedicated processors and an associated memory configured to obtain and store the measurements acquired at interface 102. In this way, such measurements may be stored and made available to other system components which may be communicatively coupled with interface 102.

System 100 further includes processing device 104 which may be configured to receive measurements made by interface 102, and may be further configured to generate sleep parameters and stimulation parameters that may be applied to user 108. As will be discussed in greater detail below, processing device 104 is configure to receive input parameters from user 108, and generate sleep parameters that identify specific changes to be made to implement the target goals specified by the user. Moreover, processing device 104 is further configured to generate stimulation parameters that are configured to identify specific sets of stimuli to be applied to implement the identified changes underlying the target goals. In various embodiments, the stimulation parameters may be included in a stimulation program which may be used to generate one or more control signals. In various embodiments, the generation of sleep parameters may include the translation of qualitative goals identified by user 108 to quantitative goals that may be mapped to specific stimulation parameters. Moreover, processing device 104 may be configured to retrieve measurement data from one or more data sources, which may be a memory device or a database system, and is further configured to retrieve measurement data obtained from the user.

As will also be discussed in greater detail below, processing device 104 is further configured to generate one or more result objects that may be included in a user interface and displayed in a display device. In various embodiments, the result objects are configured to represent a summary of the results of the application of a custom sleep program. More specifically, the result objects may be configured to represent a result or effect of the application of stimulation parameters that were generated based on identified target sleep goals. Accordingly, processing device 104 is additionally configured to generate a user interface, such as a control panel, that is configured to display an output to a user, and receive an input form the user via one or more data fields. As will be discussed in greater detail below, the user interface is configured to include various user interface elements that are configured to receive input parameters representative of target sleep goals. In some embodiments, processing device 104 includes memory device 112 which is configured to store quality assessment metrics and result objects, such as reports, generated by processing device 104.

In some embodiments, system 100 includes controller 106 which is configured to generate one or more control signals for interface 102, and is also configured to receive measurements from interface 102. Accordingly, controller 106 may be configured to implement and control the application of one or more stimulation programs and underlying stimulation parameters. In various embodiments, controller 106 is communicatively coupled with interface 102, and processing device 104. Accordingly, controller 106 is configured to received inputs from various other system components, and generate signals provided to interface 102 based, at least in part on such inputs. As will be discussed in greater detail below, such outputs may be used to provide actuations to the brain coupled with interface 102. For example, outputs generated by controller 106 may be used to stimulate the brain via one or more components of interface 102. In this way, controller 106 may provide stimuli to the brain via interface 102, may receive sleep information via other components such as processing device 104, and may generate stimuli based on such received information.

In some embodiments, controller 106 is configured to implement combined control of pharmacological and stimulation inputs. Accordingly, controller 106 may be configured to modify stimulation inputs based on an expected effect of one or more pharmacological agents that may be administered in conjunction with the stimulation. In this way, controller 106 may modify and control administration of stimuli via interface 102 based on an identified pharmacological regimen. In various embodiments, controller 106 is optionally included in system 100. For example, system 100 might not include controller 106, and such generation of control signals and receiving of measurements may be implemented by processing device 104.

Figure 2:
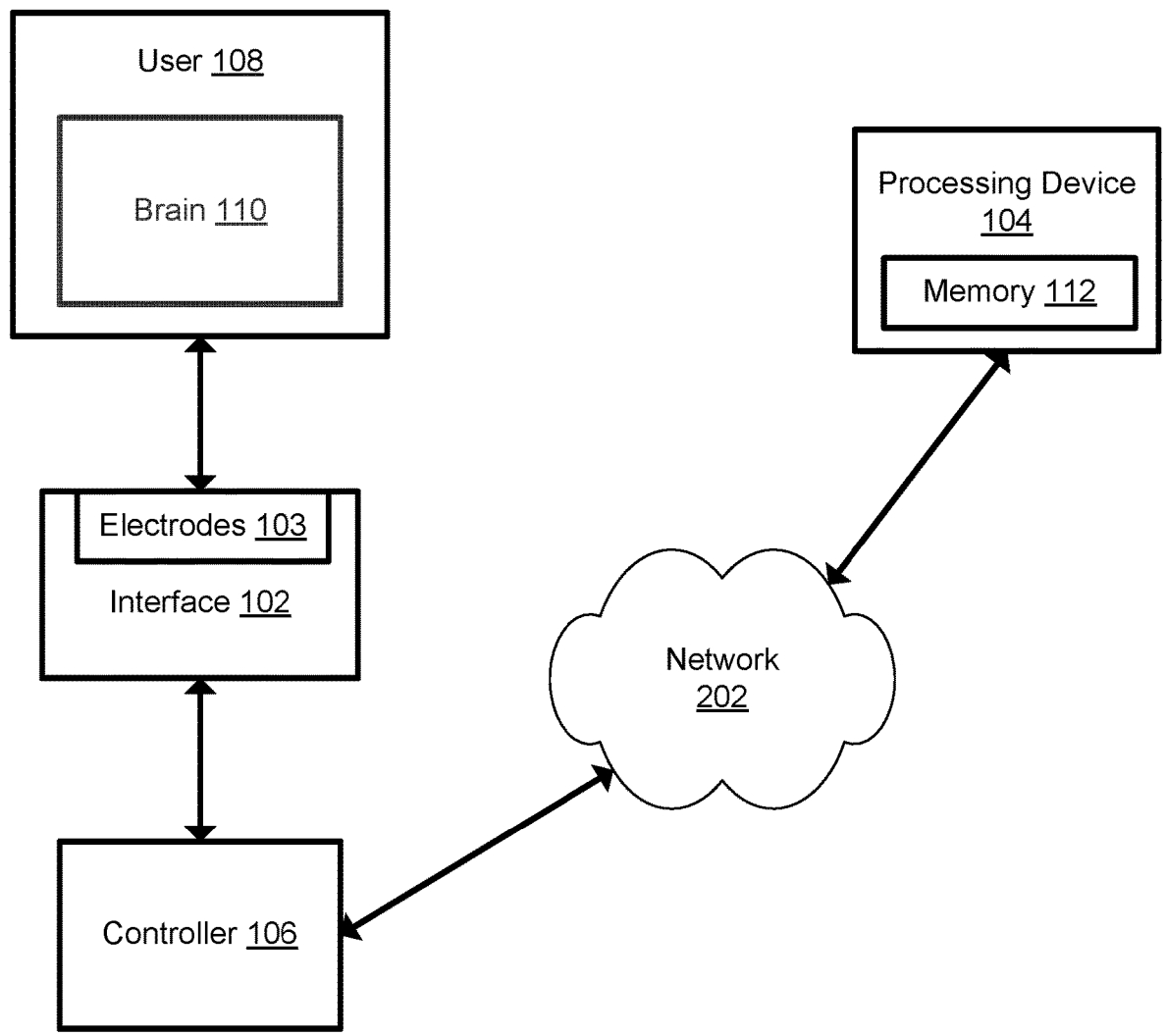
FIG. 2 illustrates another example of a system for the implementation of custom sleep parameters, configured in accordance with some embodiments.

FIG. 2 illustrates another example of a system for the implementation of custom sleep parameters, configured in accordance with some embodiments. As similarly discussed above, a user may identify target goals for their sleep profile, and subsequently have a stimulation program generated that is specifically configured to the user and the user's sleep profile. Moreover, systems, such as system 200, may include components such as interface 102, processing device 104, and controller 106, which may be coupled to a user, such as user 108.

As shown in FIG. 2, components of system 200 may be implemented in a distributed manner. For example, controller 106 may be collocated with user 108 and may be communicatively coupled to processing device 104 via a communications network, such as network 202. In this way, controller 106 may be implemented as a wireless device, such as a wearable device, at user 108, processing device 104 may be implemented remotely in a data processing system, and communications between controller 106 and processing device 104 may be handled via a network 202, which may be the internet. In this way, processing device 104 may be implemented as a personal computer or mobile device located near user 108, or processing device may be implemented as part of a distributed computing platform configured to provide sleep profile enhancement as a Software as a Service (Saas) platform.

Figure 3:
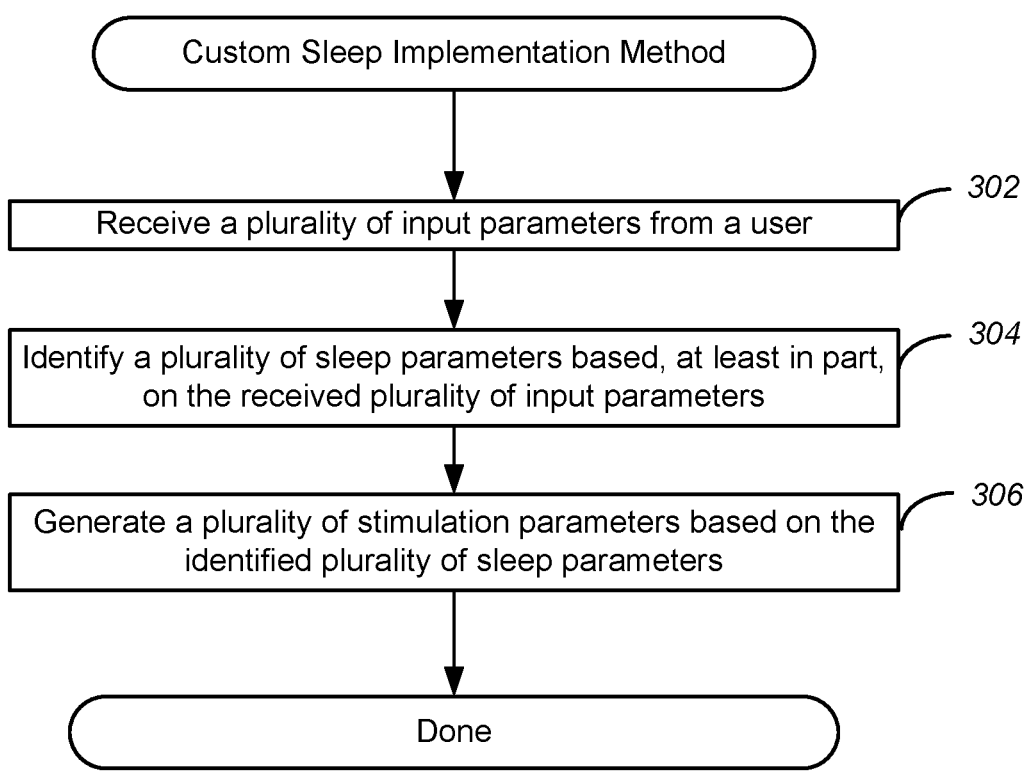
FIG. 3 illustrates an example of a flow chart of a method for the implementation of custom sleep parameters, implemented in accordance with some embodiments.

FIG. 3 illustrates an example of a flow chart of a method for the implementation of custom sleep parameters, implemented in accordance with some embodiments. As will be discussed in greater detail below, a method, such as method 300, may enable a user to identify target goals for their sleep profile, and subsequently have a stimulation program generated that is specifically configured to the user and the user's sleep profile, and configured to implement the identified changes to achieve the target goals for their sleep profile.

Accordingly, method 300 may commence with operation 302 during which a plurality of input parameters may be received from a user. In various embodiments, the input parameters are parameters that are configured to identify particular aspects of a user's sleep profile that the user intends to adjust or modify. As will be discussed in greater detail below, a user's sleep profile may characterize various aspects and signatures of the user's sleep pattern. Accordingly, the input parameters may identify various qualitative aspects of the user's sleep profile that the user intends to adjust, and further identifies the intended changes that the user would like to make.

Method 300 may proceed to operation 304 during which a plurality of sleep parameters may be identified based, at least in part, on the received plurality of input parameters. In various embodiments, the sleep parameters are configured to identify specific aspects, such as biomarkers, of the user's sleep profile that should be adjusted. Accordingly, during operation 304 specific biomarkers may be identified, as well as desired changes to such biomarkers.

Method 300 may proceed to operation 306 during which a plurality of stimulation parameters may be generated based on the identified plurality of sleep parameters. In various embodiments, the plurality of sleep parameters is configured to identify specific stimulation protocol that may be applied to implement the identified changes represented by the input parameters and the sleep parameters. Accordingly, the stimulation parameters may be used to generate control signals for the purposes of implementing the appropriate stimuli, as will be discussed in greater detail below.

Figure 4:
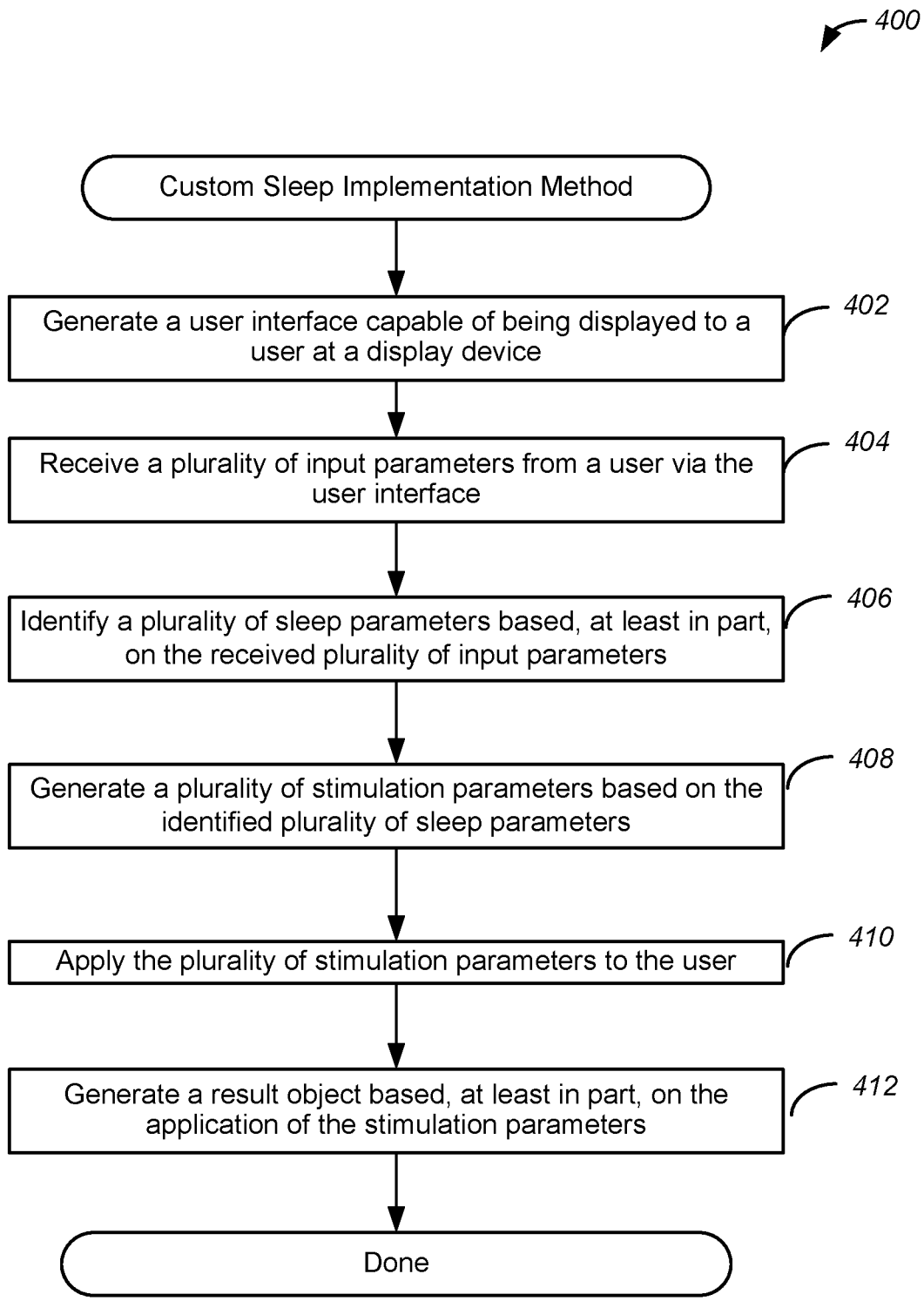
FIG. 4 illustrates another example of a flow chart of a method for the implementation of custom sleep parameters, implemented in accordance with some embodiments.

FIG. 4 illustrates another example of a flow chart of a method for the implementation of custom sleep parameters, implemented in accordance with some embodiments. As similarly discussed above a user may identify target goals for their sleep profile, and a stimulation program may be generated based on such identified target goals. As will be discussed in greater detail below, a method, such as method 400, may enable the usage of a user interface to facilitate the process, and the stimulation program may be used to provide stimulation to the user and generate a report after the application of such stimulation.

Accordingly, method 400 may commence with operation 402 during which a user interface may be generated, and the user interface may be capable of being displayed in a display device. In various embodiments, the user interface is configured to include one or more user interface elements configured to receive one or more inputs from the user. For example, the user interface may include data fields into which the user may enter text. The user interface may further include drop down menus through which the user may select one of a predetermined set of inputs. The user interface may also include sliders through which the user may select an input based on a sliding scale between two values.

In various embodiments, the user interface is configured to provide the user with a display of a plurality of aspects of the user's sleep profile that may be adjusted to implement one or more sleep goals. For example, the user interface may include a portion representing sleep latency, as well as a portion representing sleep quality. The user interface may also include portions representing more specific aspects such as sleep onset, specific sleep stage onset latency (N2 onset, N3 or deep sleep onset), total sleep duration, specific sleep stage duration, specific sleep stage duration as a % of total sleep, as well as sleep cycle durations. For example, a portion may represent a duration of a random eye movement (REM) sleep cycle. In another example, the portion may represent a duration of NREM (non REM) sleep stages. In another example, a portion could be used to specify overall sleep efficiency (total sleep time over total bed time). The user interface may also be used to specify the slow wave sleep enhancement. In this way, a particular user interface element may be generated for one or more of the above-referenced aspects of the user's sleep profile.

Moreover, each user interface element associated with each aspect of the user's sleep profile is configured to include a component configured to receive an input, such as a data field or a slider as discussed above, so that a user may provide an input that identifies a desired change to a particular aspect of the user's sleep profile. For example, a user interface component associated sleep latency may be adjusted to identify a change indicating the user wishes to decrease the time it takes the user to fall asleep. One or more changes to other parameters may also be displayed, such as a trade-off between two or more aspects of the user's sleep profile. Returning to a previous example, the user may reduce an amount of time taken to fall asleep, and this may cause an estimated reduction in the quality of the user's sleep, which may also be displayed in the user interface. In some embodiments the sleep profile parameters may be provided with a reference/baseline range which may be generated based on previous measurements for the user, or generated based on group distributions of these parameters for similar individuals, as may be determined based on biological parameters, such as age, gender, ethnicity, and health condition. The user interface may allow the user to specify their target relative to the reference/baseline ranges. For example, the user interface may be configured to present the user with sleep parameter distribution ranges based on the user's age (a sleep age profile), and let the user specify a relative sleep age of few months younger than their biological age.

Method 400 may proceed to operation 404 during which a plurality of input parameters may be received from a user. Accordingly, as discussed above, the user may provide the input parameters via the user interface, and such input parameters are configured to identify particular aspects of a user's sleep profile that the user intends to adjust or modify. Accordingly, as discussed above, the input parameters identify various qualitative aspects of the user's sleep profile that the user intends to adjust, and further identifies the intended changes that the user would like to make.

Method 400 may proceed to operation 406 during which a plurality of sleep parameters may be identified based, at least in part, on the received plurality of input parameters. As similarly discussed above, the sleep parameters are configured to identify specific aspects, such as biomarkers, of the user's sleep profile that should be adjusted. In various embodiments, biomarkers may be specific aspects of a user's sleep profile that are specific to the user's biological activity, such as a ratio of band activities, shifts in frequency spectra of activity, and a dominant resonant map of the user. Accordingly, during operation 406 specific biomarkers of the user's sleep profile may be identified, as well as desired changes to such biomarkers. Accordingly, as will be discussed in greater detail below with reference to FIG. 5, inputs provided by the user which may be represented by general descriptors may be mapped to specific biological markers and signatures of the user's sleep profile, and target changes to the biomarkers may be identified and represented in the plurality of sleep parameters.

Method 400 may proceed to operation 408 during which a plurality of stimulation parameters may be generated based on the identified plurality of sleep parameters. As similarly discussed above, the plurality of sleep parameters is configured to identify specific stimulation protocol that may be applied to implement the identified changes represented by the input parameters and the sleep parameters. Accordingly, the stimulation parameters may be used to generate control signals for the purposes of implementing the appropriate stimuli. In some embodiments, stimulation parameters may be identified based on models generated using machine learning algorithms. For example, sleep models may be developed as functional or phenomenological input-output models that can include machine learning algorithms, such as multi-variate regression, support vector machines, classifiers, deep learning neural networks, hierarchical Bayesian techniques, that are configured to learn the underlying behavior. Accordingly, previous treatment measurement data may be used to train the algorithms.

In some embodiments, the inputs to these models may include physiological measurements (such as the electrical activity, heart activity, EOG, movement), self-reported measurements, and the treatment parameters, such as the stimulation modality, and the specific stimulation parameters, such as intensity and frequency. Moreover, inverse models may be generated based, at least in part, on the above models, and such inverse models may be used to predict various treatment parameters based on the desired sleep targets. These inverse models may also be customized using data specific to an individual, and from multiple treatment sessions.

Method 400 may proceed to operation 410 during which the plurality of stimulation parameters may be applied to the user. Accordingly, during a period of sleep, the stimulation parameters may be applied to the user as a sleep program configured to implement the identified changes. For example, specific stimulation frequencies (slow wave frequencies in 0.5-2 Hz, theta wave frequencies in 4-8 Hz, and alpha wave frequencies in 8-12 Hz) may affect specific changes in the user's sleep to achieve the target sleep goals. For example, if a reduced sleep latency is desired, stimulation may be applied at specific frequency band to increase the speed with which the user falls asleep. For enhancing the slow wave activity during sleep, other stimulation frequency bands can be used. Yet another frequency band stimulation can be used to improve the NREM sleep duration. In other examples, the duration of stimulation or the intensity of stimulation can impact the onset of sleep and the total sleep duration. In this way, stimulation parameters may be applied to the user while the user sleeps to implement multiple target goals for the user's sleep profile. Moreover, measurement data may also be obtained while the user sleeps. Accordingly, measurement data may be obtained to monitor the effect of the applied stimulation program.

Method 400 may proceed to operation 412 during which a result object may be generated based, at least in part, on the application of the stimulation parameters. Accordingly, the measurement data as well as previous sleep data may be retrieved and used to generate one or more result objects that represent a result of the applied stimulation. For example, if reduced sleep latency was desired, the measurement data may be used to determine how long it took the user to fall asleep. This may be compared against a similar determination made on the user's previous sleep data. The difference between the times may be represented as a result included in a result object that is capable of being displayed in the user interface. In this way, the user may be provided with a report of how effective the applied stimulation program was, and how close the user has come to the identified target goals.

Figure 5:
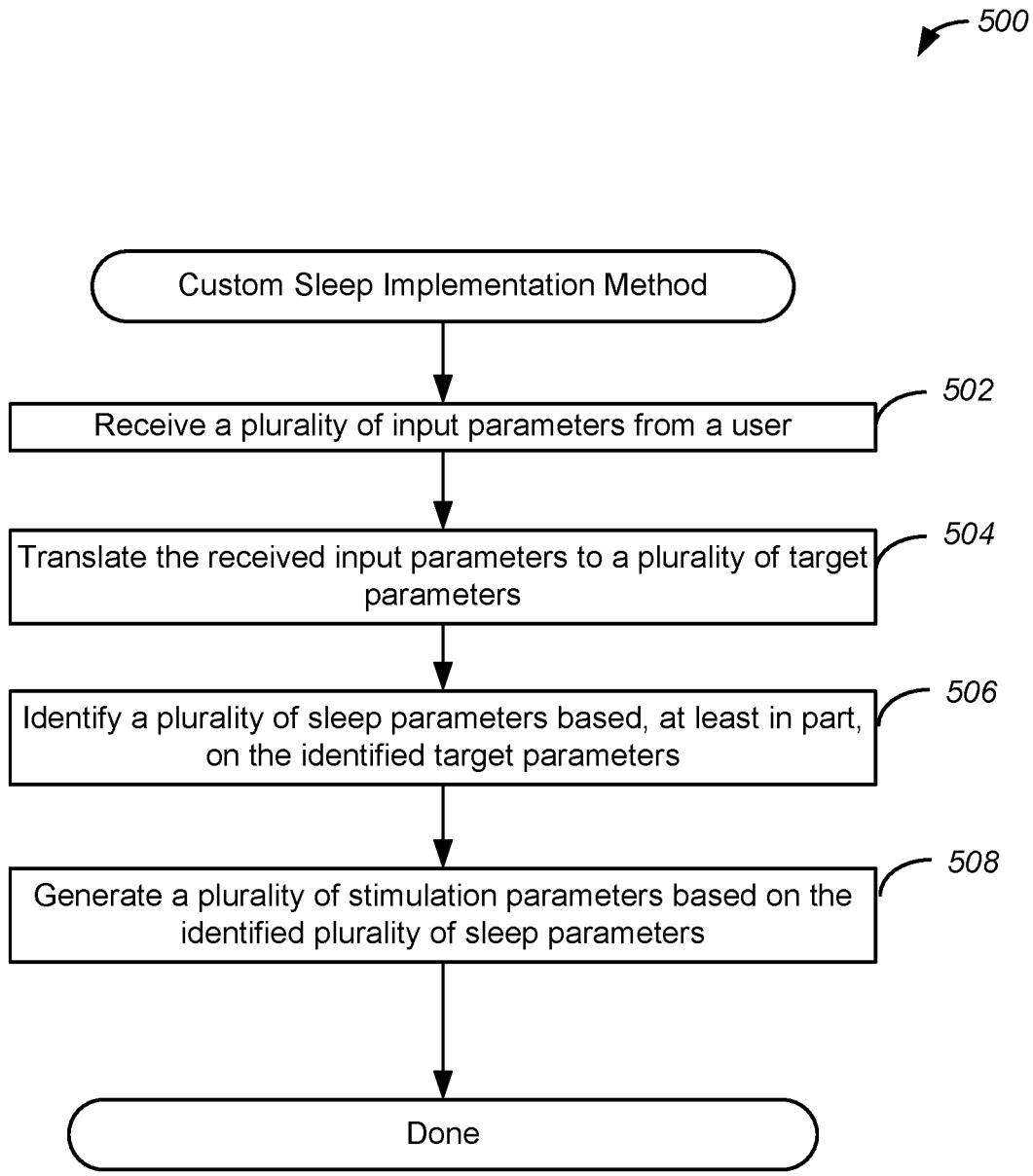
FIG. 5 illustrates an additional example of a flow chart of a method for the implementation of custom sleep parameters, implemented in accordance with some embodiments.

FIG. 5 illustrates an additional example of a flow chart of a method for the implementation of custom sleep parameters, implemented in accordance with some embodiments. As similarly discussed above a user may identify target goals for their sleep profile, and a stimulation program may be generated based on such identified target goals. As will be discussed in greater detail below, a method, such as method 500, may use one or more processing devices to translate qualitative goals to quantitative goals, and thus enhance the ease with which the user is able to identify and implement target goals for the user's sleep profile.

Accordingly, method 500 may commence with operation 502 during which a plurality of input parameters may be received from a user. As similarly discussed above, the input parameters are parameters that are configured to identify particular aspects of a user's sleep profile that the user intends to adjust or modify. Moreover, the input parameters may identify various qualitative aspects of the user's sleep profile that the user intends to adjust, and further identifies the intended changes that the user would like to make.

Method 500 may proceed to operation 504 during which the received input parameters may be translated to a plurality of target parameters. As stated above, the input parameters may be qualitative parameters that generally identify changes to be made to the user's sleep profile. During operation 504, each of the qualitative parameters may be mapped to one or more specific quantitative parameters, which may be specific biomarkers with associated stimulation parameters. In one example, a particular qualitative parameter that identifies a general target goal of reducing a sleep latency may be mapped to specific biomarkers corresponding to sleep latency. For example, the identified target parameters may include an amount of neural activity at a particular frequency band associated with a first stage of sleep. In this way, general qualitative goals may be translated or mapped to specific quantitative aspects of the user's sleep profile, and such a translation may be implemented based on a previously determined mapping stored in a storage device. In some examples, the target parameters may be specified relative to group ranges. For example, the user may specify a target sleep onset and duration corresponding to a sleep age of −2 years. In this example, the specified target parameter identifies a range that corresponds to an individual who is 2 years younger than the user's biological age, as determined based on age distributions of sleep profiles aggregated from a group of users.

Accordingly, during operation 504, the specified range may be translated to a quantitative range for the target sleep onset and duration. Moreover, such generation of a mapping and implementation of a translation may be implemented based, at least in part on the identification and usage of specific biomarkers as well as the usage of sleep models discussed above, to implement the mapping and translation. Accordingly, the sleep models discussed above may be instantiated to implement the previously described mapping and translation.

Method 500 may proceed to operation 506 during which a plurality of sleep parameters may be identified based, at least in part, on the identified target parameters. As similarly discussed above, the target parameters are configured to identify specific aspects, such as biomarkers, of the user's sleep profile that should be adjusted. Accordingly, during operation 506, specific changes to the biomarkers may be identified, and sleep parameters may be generated that identify the specified changes to the biomarkers.

Method 500 may proceed to operation 508 during which a plurality of stimulation parameters may be generated based on the identified plurality of sleep parameters. As similarly discussed above, the plurality of sleep parameters is configured to identify specific stimulation protocol that may be applied to implement the identified changes represented by the input parameters and the sleep parameters. Accordingly, the stimulation parameters may be used to generate control signals for the purposes of implementing the appropriate stimuli.

Figure 6:
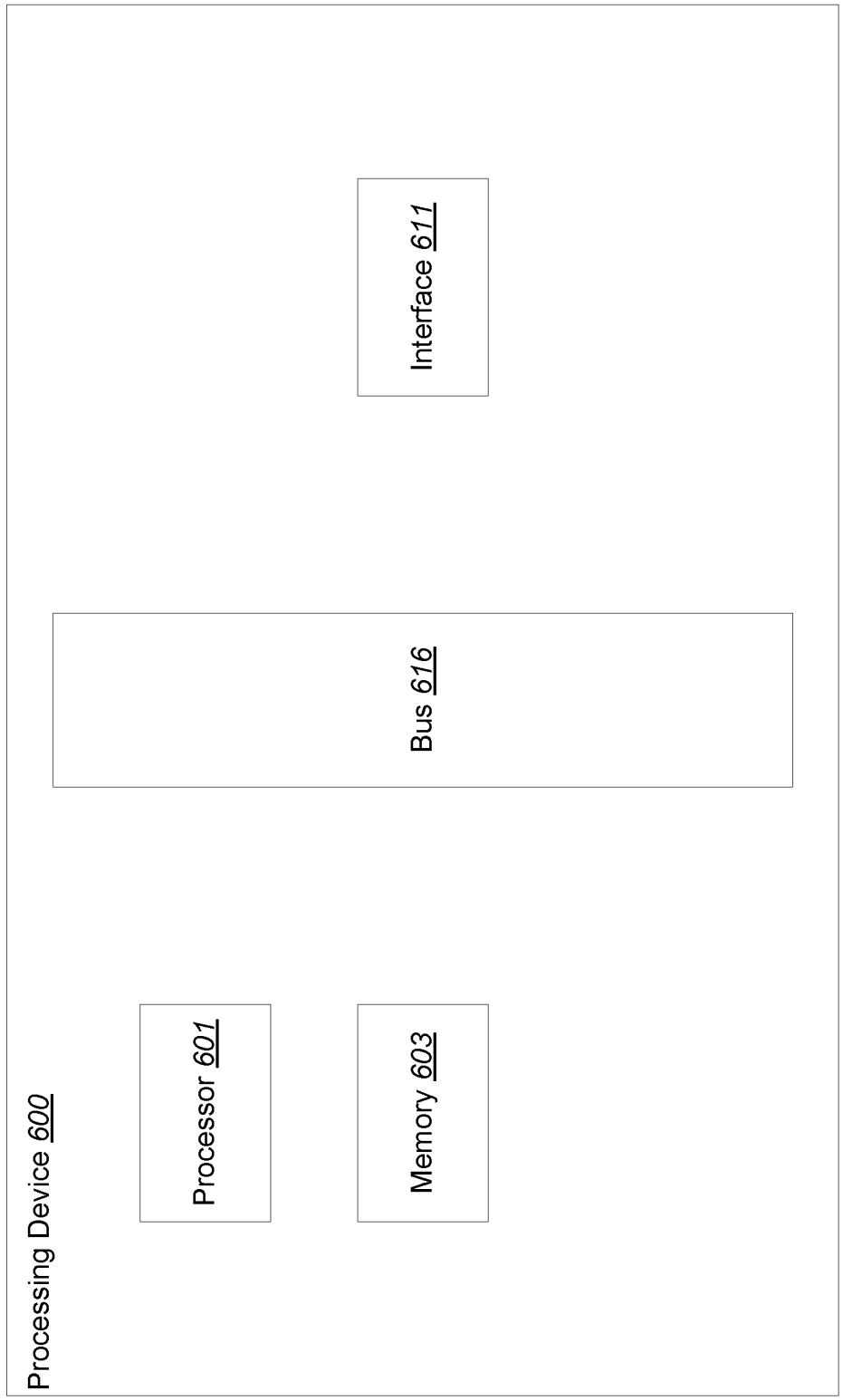
FIG. 6 illustrates an example of a processing device that can be used with various embodiments.

FIG. 6 illustrates an example of a processing device that can be used with various embodiments. For instance, the processing device 600 can be used to implement any of processing device 104 and controller 106 according to various embodiments described above. In addition, the processing device 600 shown can be implemented in conjunction with a computing system on a mobile device or on a computer or laptop, etc. According to particular example embodiments, a processing device 600 suitable for implementing particular embodiments of the present invention includes a processor 601, a memory 603, an interface 611, and a bus 616 (e.g., a PCI bus). The interface 611 may include separate input and output interfaces, or may be a unified interface supporting both operations. When acting under the control of appropriate software or firmware, the processor 601 is responsible for tasks such as sleep parameter and stimulation parameter computation and generation. Various specially configured devices can also be used in place of a processor 601 or in addition to processor 601. The complete implementation can also be done in custom hardware. The interface 611 may be configured to send and receive data packets or data segments over a network. Particular examples of interfaces the device supports include Ethernet interfaces, frame relay interfaces, cable interfaces, DSL interfaces, token ring interfaces, and the like. In various embodiments, interface 611 may also be a wired connection or a bus with appropriate communications ports.

In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as packet switching, media control and management.

According to particular example embodiments, the processing device 600 uses memory 603 to store data and program instructions and maintain a local side cache. The program instructions may control the operation of an operating system and/or one or more applications, for example. The memory or memories may also be configured to store received metadata and batch requested metadata.

Because such information and program instructions may be employed to implement the systems/methods described herein, the present invention relates to tangible, machine readable media that include program instructions, state information, etc. for performing various operations described herein. Examples of machine-readable media include memory devices such as non-volatile memory devices, volatile memory devices, and may also utilize optical media such as CD-ROM disks and DVDs, and hardware devices that are specially configured to store and perform program instructions, such as read-only memory devices (ROM) and programmable read-only memory devices (PROMs). Examples of program instructions include both machine code, such as produced by a compiler, and files containing higher level code that may be executed by the computer using an interpreter.

While the present disclosure has been particularly shown and described with reference to specific embodiments thereof, it will be understood by those skilled in the art that changes in the form and details of the disclosed embodiments may be made without departing from the spirit or scope of the disclosure. Specifically, there are many alternative ways of implementing the processes, systems, and apparatuses described. It is therefore intended that the invention be interpreted to include all variations and equivalents that fall within the true spirit and scope of the present invention. Moreover, although particular features have been described as part of each example, any combination of these features or additions of other features are intended to be included within the scope of this disclosure. Accordingly, the embodiments described herein are to be considered as illustrative and not restrictive.

What is claimed is:

1. A method, comprising:
   receiving, via a user interface, two or more input parameters associated with a sleep profile of a user, the two or more input parameters representing at least one sleep profile target;
   generating, using one or more processors of a processing device, a plurality of sleep parameters based, at least in part, on the received two or more input parameters, the plurality of sleep parameters representing two or more changes to two or more biomarkers of the user;
   generating a plurality of stimulation parameters based, at least in part, on the plurality of sleep parameters, the plurality of stimulation parameters representing electrical stimuli to a user's brain configured to implement the two or more changes for each of the two or more biomarkers of the user;
   determining a trade-off in the two or more input parameters including a change in a first input parameter of the two or more input parameters based on the receiving a second input parameter of the two or more input parameters, wherein the first input parameter includes sleep quality and the second input parameter includes sleep latency;
   displaying, with the user interface, the change in the first input parameter;
   applying stimuli to the user based, at least in part, on the plurality of stimulation parameters; and
   receiving measurement data based, at least in part, on the applying of the stimuli.

2. The method of claim 1 further comprising:
   mapping the two or more input parameters to a plurality of target parameters, the plurality of target parameters identifying the two or more biomarkers of the user.

3. The method of claim 2, wherein the mapping is generated based, at least in part, on previous measurement data.

4. The method of claim 1, wherein the two or more changes represented by the plurality of sleep parameters are configured to identify target values for the two or more biomarkers.

5. The method of claim 4, wherein the two or more biomarkers comprise a ratio of band activities and shifts in frequency spectra of activity.

6. The method of claim 4, wherein the plurality of stimulation parameters is configured to change each of one or more current values of the two or more biomarkers to the identified target values of the two or more biomarkers.

7. The method of claim 1, further comprising:
   generating a result object based, at least in part, on the measurement data, the result object representing an efficacy of the plurality of stimulation parameters.

8. The method of claim 7, wherein the efficacy of the plurality of stimulation parameters is determined based, at least in part, on the at least one sleep profile target.

9. The method of claim 1, wherein the sleep profile target includes sleep latency.

10. The method of claim 1, wherein the sleep profile target includes sleep quality.

11. The method of claim 1, wherein the sleep profile target includes sleep onset.

12. The method of claim 1, wherein the sleep profile target includes sleep stage onset latency.

13. The method of claim 1, wherein the sleep profile target includes total sleep duration, specific sleep stage duration, specific sleep stage duration as a % of total sleep, and sleep cycle duration.

14. The method of claim 13, wherein the sleep cycle duration includes a duration of a random eye movement (REM) sleep cycle.

15. The method of claim 1, wherein the sleep profile target includes overall sleep efficiency.

16. The method of claim 1, wherein the sleep profile target includes slow wave sleep enhancement.

17. The method of claim 1, further comprising displaying, via the user interface, the sleep profile of the user, wherein the sleep profile is a sleep age profile of the user.

18. The method of claim 1, wherein the sleep profile target includes user age-based demography derived targets.

19. A system comprising:
a communications interface configured to receive one or more input parameters associated with a sleep profile of a user, the one or more input parameters representing at least one sleep profile target;
a processing device configured to:
generate a plurality of sleep parameters based the received one or more input parameters, and the plurality of sleep parameters representing one or more changes to one or more biomarkers of the user;
generate a plurality of stimulation parameters based, at least in part, on the plurality of sleep parameters, the plurality of stimulation parameters representing stimuli configured to implement the one or more changes for each of the one or more biomarkers of the user;
determine a trade-off in the one or more input parameters including a change in a first input parameter of the one or more input parameters based on receiving a second input parameter, wherein the first input parameter includes sleep quality and the second input parameter includes sleep latency;
cause display on the communications user interface, the change in the first parameter;
apply stimuli to the user based, at least in part, on the plurality of stimulation parameters; and
receive measurement data based on the applying of the stimuli; and
a memory device configured to store the plurality of sleep parameters and the plurality of stimulation parameters.

20. The system of claim 19, wherein the processing device is further configured to:
map the one or more input parameters to a plurality of target parameters, the plurality of target parameters identifying the one or more biomarkers of the user.

21. The system of claim 19, wherein the one or more changes represented by the plurality of sleep parameters are configured to identify target values for the one or more biomarkers.

22. The system of claim 21, wherein the plurality of stimulation parameters is configured to change each of one or more current values of the one or more biomarkers to the identified target values of the one or more biomarkers.

23. The system of claim 19, wherein the processing device is further configured to:
generate a result object based, at least in part, on the measurement data, the result object representing an efficacy of the plurality of stimulation parameters.

24. The system of claim 23, wherein the efficacy of the plurality of stimulation parameters is determined based, at least in part, on the at least one steep profile target.

25. A device comprising:
a communications interface configured to receive one or more input parameters associated with a sleep profile of a user, the one or more input parameters representing at least one sleep profile target; and
one or more processors configured to:
generate a plurality of sleep parameters based, at least in part, on the received one or more input parameters, the plurality of sleep parameters representing one or more changes to one or more biomarkers of the user;
generate a plurality of stimulation parameters based, at least in part on the plurality of sleep parameters, and the plurality of stimulation parameters representing stimuli configured to implement the one or more changes for each of the one or more biomarkers of the user;
determine a trade-off in the one or more input parameters including a change in a first input parameter of the one or more input parameters based on receiving a second input parameter, wherein the first input parameter includes sleep quality and the second input parameter includes sleep latency;
cause display on the communications user interface, the change in the first parameter;
apply stimuli to the user based, at least in part, on the plurality of stimulation parameters; and
receive measurement data based on the applying of the stimuli.

26. The device of claim 25 wherein the one or more processors are further configured to:
map the one or more input parameters to a plurality of target parameters, the plurality of target parameters identifying the one or more biomarkers of the user.

27. The device of claim 25, wherein the one or more changes represented by the plurality of sleep parameters are configured to identify target values for the one or more biomarkers.

28. The device of claim 27, wherein the plurality of stimulation parameters is configured to change each of one or more current values of the one or more biomarkers to the identified target values of the one or more biomarkers.

29. The device of claim 25 wherein the one or more processors are further configured to:
generate a result object based, at least in part, on the measurement data, the result object representing an efficacy of the plurality of stimulation parameters.

* * * * *